United States Patent
Tipirneni (10) Patent No.: US 8,069,060 B2
(45) Date of Patent: Nov. 29, 2011

(54) SYSTEM AND METHOD FOR MANAGING MEDICAL FACILITY PROCEDURES AND RECORDS

(75) Inventor: Kishore Tipirneni, Glendale, AZ (US)

(73) Assignee: Merge Healthcare Incorporated, Milwaukee, WI (US)

(*) Notice: Subject to any disclaimer, the term of this patent is extended or adjusted under 35 U.S.C. 154(b) by 1435 days.

(21) Appl. No.: 10/905,279

(22) Filed: Dec. 23, 2004

(65) Prior Publication Data

US 2006/0143041 A1 Jun. 29, 2006

(51) Int. Cl.
*G06F 19/00* (2006.01)

(52) U.S. Cl. .................................. 705/3; 705/2

(58) Field of Classification Search ............ 705/2, 3, 705/8, 6; 600/300; 340/286.01, 286.07, 340/506, 870.11, 825.49; 707/2
See application file for complete search history.

(56) References Cited

U.S. PATENT DOCUMENTS

| | | | |
|---|---|---|---|
| 3,675,204 A | 7/1972 | Miehle et al. | |
| 5,748,907 A * | 5/1998 | Crane | 705/2 |
| 5,760,704 A * | 6/1998 | Barton et al. | 340/825.49 |
| 6,453,297 B1 | 9/2002 | Burks et al. | |
| 6,556,878 B1 | 4/2003 | Fielding | |
| 6,915,265 B1 | 7/2005 | Johnson | |
| 7,197,492 B2 * | 3/2007 | Sullivan | 707/2 |
| 7,428,494 B2 | 9/2008 | Hasan et al. | |
| 2002/0016923 A1 | 2/2002 | Knaus et al. | |
| 2002/0077865 A1 * | 6/2002 | Sullivan | 705/3 |
| 2003/0046114 A1 | 3/2003 | Davies et al. | |
| 2003/0074222 A1 * | 4/2003 | Rosow et al. | 705/2 |
| 2004/0017475 A1 | 1/2004 | Akers et al. | |
| 2004/0030586 A1 * | 2/2004 | Cucchiara et al. | 705/3 |
| 2004/0064343 A1 | 4/2004 | Korpman et al. | |
| 2004/0090333 A1 | 5/2004 | Wildman et al. | |
| 2004/0128163 A1 | 7/2004 | Goodman et al. | |
| 2004/0138925 A1 * | 7/2004 | Zheng | 705/2 |
| 2004/0220836 A1 | 11/2004 | Doherty et al. | |
| 2004/0243446 A1 | 12/2004 | Wyatt | |
| 2005/0010441 A1 * | 1/2005 | Wheeler | 705/2 |
| 2005/0060211 A1 * | 3/2005 | Xiao et al. | 705/6 |
| 2005/0071190 A1 * | 3/2005 | Herger et al. | 705/2 |
| 2005/0091338 A1 | 4/2005 | de la Huerga | |
| 2006/0004605 A1 * | 1/2006 | Donoghue et al. | 705/2 |
| 2006/0004762 A1 | 1/2006 | Berning et al. | |
| 2006/0053034 A1 * | 3/2006 | Hlathein et al. | 705/2 |
| 2006/0206011 A1 * | 9/2006 | Higgins et al. | 600/300 |
| 2007/0078856 A1 | 4/2007 | Dettinger et al. | |
| 2008/0097918 A1 | 4/2008 | Spector et al. | |
| 2009/0024417 A1 | 1/2009 | Marks et al. | |

* cited by examiner

*Primary Examiner* — Gerald J. O'Connor
*Assistant Examiner* — Natalie A Pass
(74) *Attorney, Agent, or Firm* — Michael Best & Friedrich LLP (57) ABSTRACT

The invention facilitates the efficient administration of medical offices and patient records including visual coordination of room, patient, and task status indicators. The invention also enables improved document review and transcription management.

10 Claims, 5 Drawing Sheets

SYSTEM AND METHOD FOR MANAGING MEDICAL FACILITY PROCEDURES AND RECORDS

FIELD OF INVENTION

The invention relates generally to a system and method for the efficient administration of medical offices and patient records. More particularly, the invention relates to web-based, networked software applications for managing medical offices, records, billing, calendaring and physician ordered tasks.

BACKGROUND OF INVENTION

A routine visit by a patient to a doctor typically involves numerous medical office staff members and a range of procedures and documentation. Management of the myriad tasks and records involved in such visits has long been an involved and difficult process. Doctors have traditionally relied upon staff members to retrieve patient documentation and to obtain x-rays or other information from other offices or labs. Likewise, a doctor's request for lab work, surgery, or other procedures is typically coordinated by staff members with the doctor relying on verbal or written communication with staff throughout and following patient visits.

The delay and potential for error inherent in such conventional verbal and written communications often results in unnecessary delay for patients and care providers alike. Doctors typically review patient profile documentation before an examination. More timely notice of a patient's medical profile in preparation for a patient's visit could increase patient flow-through. Additionally, paper records inevitably become incomplete or missing as portions or all of a file is moved between the front desk, examination room, labs, and offsite provider offices. Paper systems are further deficient in that they require multiple copies for simultaneous viewing of records.

With a paper system or a closed office network, Physicians may not be able to access vital patient information when they are out of the office. Likewise, prior systems typically provided limited file export capabilities, often requiring accessing and printing from a number of separate software applications or databases. File export is necessary, for example, when a patient requests a copy of all or portions of her file or when a referral specialist requests a complete history for a patient's condition.

Paper systems are inherently prone to many types of errors. Omitted or inaccurate medication records could be potentially life threatening. For example, an omitted medication on a chart may lead to a harmful drug interaction. Additionally, omitted or inaccurate billing records may lead to lost charges for services. For example, a physician may perform a number of billable services and forget to record each service on a paper chart ticket.

There has, therefore, been a movement in the industry towards electronic records keeping and office management and real time interaction with staff and records databases. Most so called electronic management systems require proprietary client software installed on individual work stations making remote access from home or offsite labs difficult. Typically, efficient office management requires a number of separate proprietary systems, creating redundancy and incompatibility issues. There is, therefore, a need for an efficient, integrated, web-based office management product providing improved user communications and user friendly, secure access from any internet ready workstation.

SUMMARY OF INVENTION

The invention generally provides a web-based office management software application that yields improved efficiency and communications between physicians, staff members, and lab technicians. An exemplary embodiment includes a web-based office management software application, hosted on an internet accessible server. The server connects various user terminals to a central records database and to the other user terminals. Color coordination (or any other indicia) of examination room identifiers on user displays continually (or intermittently) conveys at least one of whether a room has been assigned to a patient, who the attending physician is, what tasks the physician has ordered (e.g. x-rays, casts, blood tests), and the status of those tasks. For example, a "room identifier" color (or other indicator) may change upon completion of each of multiple ordered tasks. Reversion of the room identifier color to the physician's color indicates that all (or a certain portion of) ordered tasks have been completed. The server may be accessible remotely from internet ready terminals including wireless or portable terminals such as a doctor's tablet PC or other handheld device. The portability and connectivity of physician terminals allows physicians to be in real time contact with staff and technicians with immediate access to patient records. Accordingly, physicians may request procedures, records, prescriptions, and even schedule follow-up matters without leaving the examination room and without relying on verbal communication or paper requests to staff members.

Other features of the invention include improved records keeping allowing users to upload documents and images to patient files to be viewed and supplemented by other authorized users. Integrated document management applications allow users to place documents such as, for example, faxes, transcriptions and completed task reports, in electronic user mailboxes for user review or directly in patient files. This system improves the workflow and patient safety in medical care facilities. Wait time may thus be reduced for both patients and medical staff while safety may be increased by more reliable communication and record keeping.

BRIEF DESCRIPTION OF THE DRAWINGS

A more complete understanding of the invention may be derived by referring to the detailed description and claims when considered in connection with the Figures, wherein like reference numbers refer to similar elements throughout the Figures, and:

DETAILED DESCRIPTION

The detailed description of exemplary embodiments of the invention herein makes reference to the accompanying drawings, which show the exemplary embodiment by way of illustration. While these exemplary embodiments are described in sufficient detail to enable those skilled in the art to practice the invention and reveal the best mode of doing so, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases.

In general, the invention provides efficient integration of medical facilities management, patient records management, patient calendaring and billing, task management, and user communication. The invention increases patient flow-through by optimizing communications between various users by color coding room identifiers according to room/patient status and the status of associated tasks ordered by the attending physician.

Figure 1:
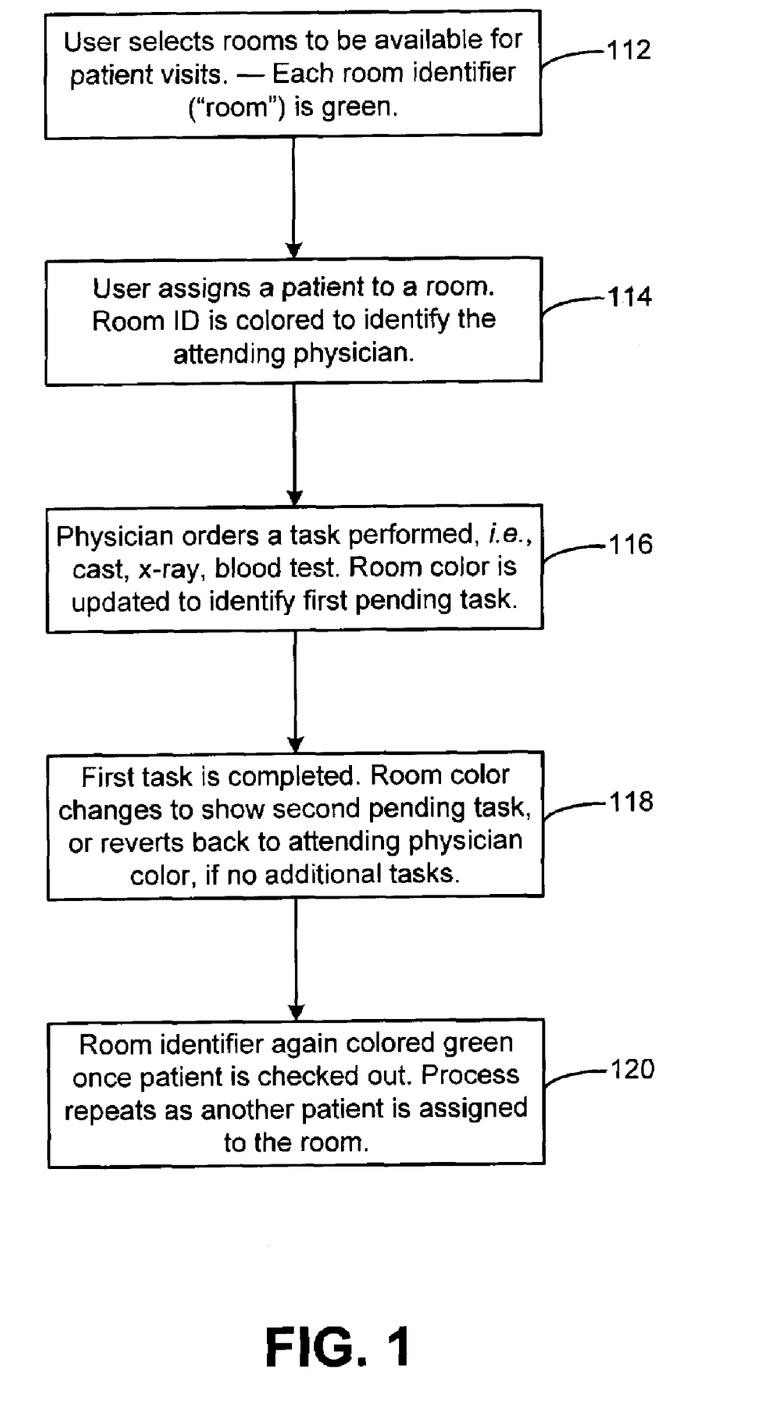
FIG. 1 is a block diagram showing various components of an exemplary medical office network according to the invention.

Turning to the drawings, FIG. 1 illustrates an exemplary medical facility management network 200, including a host server 202, various user interface terminals 204 A-F, a patient records database 206, a wireless access point 208, an input digitizer 214 and connections to the internet 210 and other inputs such as a fax server 212. Server 202 includes a processor for processing digital data and a memory coupled to said processor for storing digital data, and an application program stored in said memory and accessible by said processor for directing processing of digital data by said processor.

"Users" may include any authorized person, such as, for example, any physician, office or medical staff member, technician, care provider, nurse, assistant, transcriptionist, or any other medical professional, or administrator. As used herein, the terms "user", "physician", "technician", "staff", "patient", or "assistant" may be used interchangeably with each other, and each shall mean any appropriate person, entity, machine, hardware, software or business. Each user is equipped with a computing device in order to interact with the system. Office and medical staff have computing units in the form of personal computers, although other types of computing units may be used including laptops, notebooks, hand held computers, set-top boxes, cellular telephones, touch-tone telephones and the like. The medical office has access to a computing unit implemented in the form of a computer-server, although other implementations are contemplated by the invention, such as a mini-computer, a PC server, a network of computers located in the same or different geographic locations, or the like.

User terminals 204 may include any hardware and/or software suitably configured to connect to server 202 through any networking means known in the art. While the disclosure makes frequent reference to "terminal", practitioners will appreciate that any computing device capable of transmitting data to and receiving data from one or more other computing devices may be equally applicable. Exemplary user terminals 204 may include a front desk terminal 204 A, an exam room terminal 204 B, an x-ray lab terminal 204 C, a cast or blood lab terminal 204 D, a wireless Tablet PC terminal 204 E, and a remote terminal 204 F connected to the network through the internet.

Any of terminals 204 A-F may be connected to server 202 through a private office network, through the public internet, or by means of a bluetooth, cellular, or wi-fi access point 208 or other wireless technologies. Access point 208 may include use of WEP keys or any other security means known or developed in the art. Additional security features are discussed later. Portable Tablet PC terminal 204 E is particularly useful where physicians or staff are attending to multiple patients in multiple rooms and require immediate access to patient records and instant communication with other staff members and technicians. Portable terminals like Tablet PC 204 E eliminate redundant activities such as converting paper notes into electronic documents for attachment to patient files. Notes, and even dictations may be instantly captured and associated electronically with a patient file and may then be processed by staff members even before the office visit is completed.

Remote terminal 204 F may be any offsite terminal such as, for example, a physicians home computer, a computer at a hotel, or a computer at another office, clinic, or hospital. A significant advantage of a web-based application is that it may be accessed from any internet ready terminal without the need to download proprietary software.

As those skilled in the art will appreciate, user terminals may include an operating system (e.g., Windows XP, NT, 95/98/2000, OS2, UNIX, Linux, Solaris, MacOS, etc.) as well as various conventional support software and drivers typically associated with computers. The terminals may include any suitable personal computer ("PC"), handheld device, tablet PC, network computer, workstation, minicomputer, cell-phone, mainframe or the like. A user terminal can be in a home or business environment or may be a handheld device with access to a network. In an exemplary embodiment, access is through a network or the Internet through a commercially-available web-browser software package.

With continued reference to FIG. 1, server 202 may host a fax delivery application (such as Right Fax) or, alternatively may be connected to a separate fax server 212. Fax server 212 may include any hardware and/or software suitably configured to send and receive electronic transmissions of documents. Fax server 212 may be implemented through commercially available hardware and/or software, through custom hardware and/or software components, or through a combination thereof. Fax server 212 may be integrated within server 202 or may reside in any separate entity. Received faxes may be delivered electronically to user mailboxes for review and optionally for attachment to corresponding patient records. Alternatively, character recognition may be used to automatically associate incoming messages with certain user mailboxes or patient files based on recognition of any number of character sets such as a patient name, patient file number, or combinations of patient demographic information. Additionally, input digitizer 214 may be coupled to server 202 for inputting digital data Patient records database 206 may include any hardware and/or software suitably configured to store patient records and associated files including, for example, visit notes, transcriptions, reports, prescriptions, x-rays, history, bills, intake documents, insurance information and the like. One skilled in the art will appreciate that the patient records database may employ any number of databases in any number of configurations. Authorized users may choose to view, edit or export any part or all of a patient record from patient records database 206 to a user mailbox, to a particular user terminal, to a printer or through any other means known in the art.

User access or authorization to view or alter information stored within the patient records database 206 may depend on various classifications of patient information. For example, a more open class of information may consist of, for example, a patient's name, address, phone number and/or time and date of medical visit and/or the like. On the other hand, a more closed class of confidential patient information may include, for example, insurance policy information, and reason for seeking the medical care, or any other information related to patient treatment. Those skilled in the art may choose equally suitable definitions which are contemplated for use herein.

Classified information may be stored within the patient records database 206 correlative to a distinct patient identifier. The classified information and the distinct patient identifier may be recorded in a single data storage location in real-time as the patient provides the information. The single data storage location may then be used to track the medical facility patient traffic, recall a patient visit, or the like.

Patient database 206 as discussed herein may include any type of structure, such as relational, hierarchical, graphical, object-oriented, and/or other database configurations. Various databases used herein may store: patient data; care provider data; medical institution data; and/or like data useful in the operation of the invention. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. Any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

Data sets may include security information annotations for establishing various access levels. The access levels may, for example, be configured to permit only certain individuals, levels of employees, companies, or other entities to access data sets. Furthermore, security information or other access restriction parameters may restrict/permit only certain user specific actions such as accessing, modifying, and/or deleting data sets as appropriate.

A patient's basic information (e.g., name, address, insurance number, reason for visit, and any other minimal information related to the patient visit) may be collected, anonymized, separated, analyzed, categorized, or minimally processed prior to the patient receiving medical attention. Office staff may provide updated records and information, such as lab results or intake documentation to the doctor without interrupting the examination and without need for verbal communication.

User or patient authentication may include use of any device, code, number, letter, symbol, digital certificate, smart chip, digital signal, analog signal, biometric or other identifier/indicia suitably configured to allow the authenticated access, interaction or communication with the system (e.g., one or more of an authorization/access code, personal identification number (PIN), Internet code, other identification code, and/or the like). User identification may optionally be located on or associated with a card, embossed card, smart card, magnetic stripe card, bar code card, transponder, or radio frequency card. The system may include or interface with any of the foregoing cards or devices, or a fob having a transponder and RFID reader in RF communication with the fob. The system may include any device having a transponder which is configured to communicate with RFID reader via RF communication. Typical devices may include, for example, a key ring, tag, card, cell phone, wristwatch or any such form capable of being presented for interrogation.

Moreover, any system, computing unit or device discussed herein may include a "pervasive computing device," which may include a traditionally non-computerized device that is embedded with a computing unit. The user or patient identification may be distributed and stored in any form of plastic, electronic, magnetic, radio frequency, wireless, audio and/or optical device capable of transmitting or downloading data from itself to a second device.

As used herein, the term "network" shall include any electronic communications means which incorporates both hardware and software components of such. Communication among the parties in accordance with the invention may be accomplished through any suitable communication channels, such as, for example, a telephone network, an extranet, an intranet, Internet, point of interaction device (point of sale device, personal digital assistant, cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, although the invention is frequently described herein as being implemented with TCP/IP communications protocols, the invention may also be implemented using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

As used herein, "transmit" may include sending electronic data from one system component to another over a network connection. Additionally, as used herein, "data" may include encompassing information such as commands, queries, files, data for storage, and the like in digital or any other form.

The invention contemplates uses in association with web services, utility computing, pervasive and individualized computing, security and identity solutions, autonomic computing, commodity computing, mobility and wireless solutions, open source, biometrics, grid computing and/or mesh computing.

One skilled in the art will also appreciate that, for security reasons, any databases, systems, devices, servers or other components of the invention may consist of any combination thereof at a single location or at multiple locations, wherein each database or system includes any of various suitable security features, such as firewalls, access codes, encryption, decryption, compression, decompression, and/or the like.

The computers discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and the like. A server may include a web service that receives a request from a web server, the request including a URL (http://yahoo.com/stockquotes/ge) and an IP address (123.56.789). The web server retrieves the appropriate web pages and sends the data or applications for the web pages to the IP address. Web services are applications that are capable of interacting with other applications over a communications means, such as the internet. Web services are typically based on standards or protocols such as XML, SOAP, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference.

The invention may be described herein in terms of functional block components, screen shots, optional selections and various processing steps. It should be appreciated that such functional blocks may be realized by any number of hardware and/or software components configured to perform the specified functions. For example, the invention may employ various integrated circuit components, e.g., memory elements, processing elements, logic elements, look-up tables, and the like, which may carry out a variety of functions under the control of one or more microprocessors or other control devices. Similarly, the software elements of the invention may be implemented with any programming or scripting language such as C, C++, Java, Macromedia ColdFusion, Microsoft Active Server Pages, COBOL, assembler, PERL, Visual Basic, SQL Stored Procedures, extensible markup language (XML), with the various algorithms being implemented with any combination of data structures, objects, processes, routines or other programming elements. Further, it should be noted that the invention may employ any number of conventional techniques for data transmission, signaling, data processing, network control, and the like. Still further, the invention could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As will be appreciated by one of ordinary skill in the art, the invention may be embodied as a customization of an existing system, an add-on product, upgraded software, a stand alone system, a distributed system, a method, a data processing system, a device for data processing, and/or a computer program product. Accordingly, the invention may take the form of an entirely software embodiment, an entirely hardware embodiment, or an embodiment combining aspects of both software and hardware. Furthermore, the invention may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The invention is described herein with reference to screen shots, block diagrams and flowchart illustrations of methods, apparatus (e.g., systems), and computer program products according to various aspects of the invention. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

Figure 2:
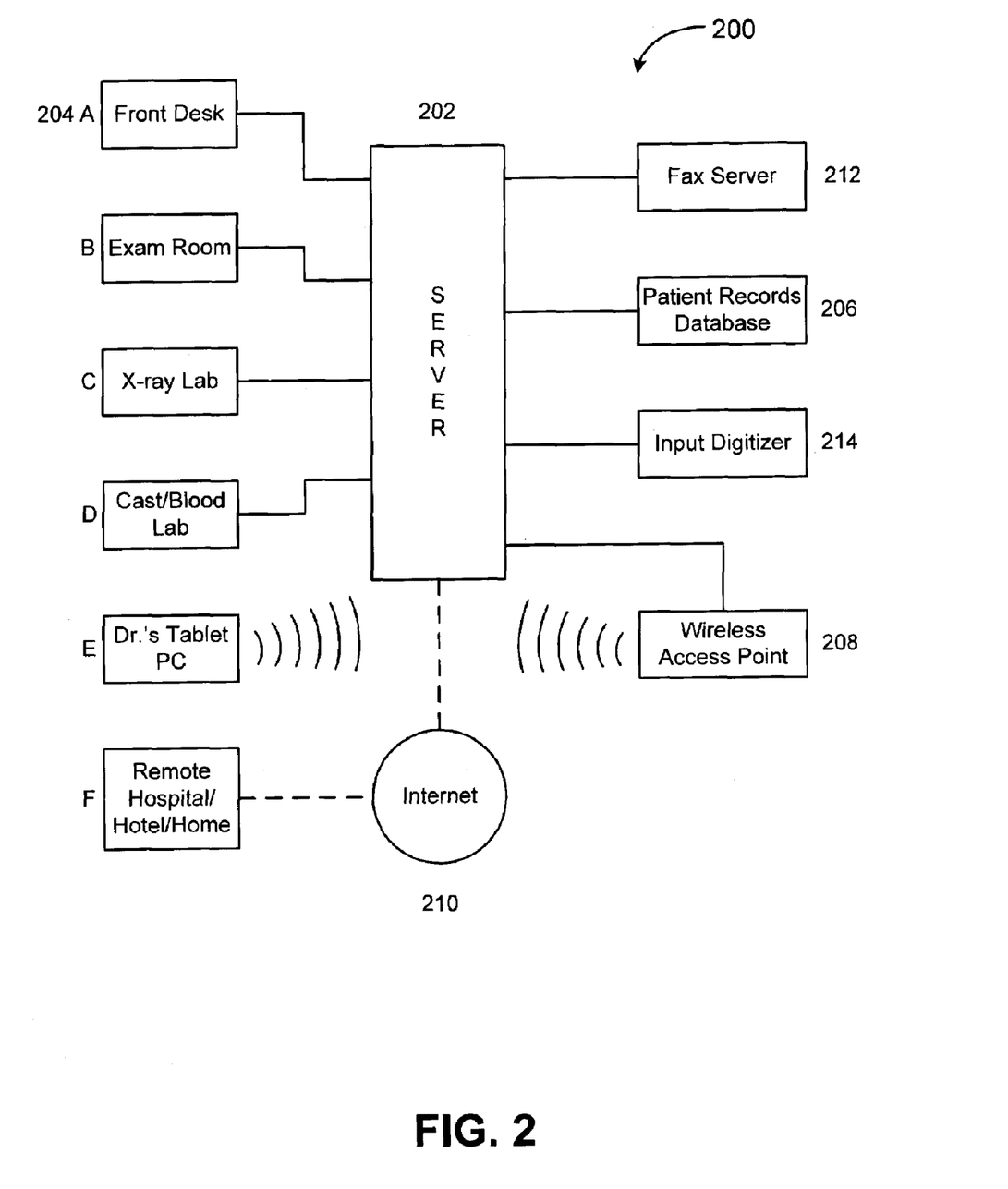
FIG. 2 is an exemplary flow chart illustrating color coordination steps in accordance with an exemplary embodiment of the invention.

Referring now to FIG. 2, a flow chart depicts the use of color coding according to an exemplary embodiment of the invention. A user such as a front desk attendant or physician selects the available examination rooms that are to be used for patient visits that day. (step 112). All available rooms may be listed, for example, as selectable radio buttons. Selected rooms may be initially coded green to indicate that they are vacant. In this example, the user then assigns a checked-in patient to room three. (step 114). The assigned room is then coded to indicate the particular physician that will be attending to the patient assigned to that room. This is helpful in clinics with numerous physicians and numerous examination rooms. Thus, users at any terminal may instantly know which rooms are occupied and what physicians are assigned to each room.

The attending physician may order certain tasks, such as, for example, x-rays, injections, casts, therapy, blood tests, or any number of other procedures. (step 116). Each task or procedure is associated with a particular color. The color may be updated to reflect a series of tasks as they are requested, completed, and reviewed. (step 118). Coding the examination room identifier to correspond with a particular task or procedure allows technicians to efficiently receive and carry out physician orders. Different users may be presented with different color schemes. For example, if a physician orders a blood test (corresponding to blue) and x-rays (corresponding to yellow) for a patient in room three, the testing lab terminal would show room three coded blue while the x-ray lab terminal would show room three coded yellow. The physician's personal terminal may show the room as either blue or yellow according to the preferences set by the physician as to the priority (chronological, urgent, longest lead time, etc.) to be given assigned tasks. For example, if rooms are coded according to the first order given, the physician terminal room identifier would remain blue until the blood tests were completed. If the x-rays were not yet completed, the room would then appear yellow until the x-rays were also completed. When both tasks are completed, the room color reverts back to the physician's identifying color. Thus, the physician and staff may instantly know the status of ordered tasks.

Additionally, charges associated with each task may be automatically entered on the checkout sheet for billing. Automatic or "passive" charge entry for each task or billable service, thus, ensures that all billable charges during a patient visit are accurately captured and recorded.

Selecting a particular room identifier may show all tasks currently associated with that room. This system improves office efficiency as multiple users with various responsibilities relating to a patient assigned to a room may independently be notified of and report on tasks assigned to them. Upon completion of patient check-out and all assigned tasks, the room identifier is again displayed as vacant. (step 120). Staff may also manually reset room three again to reflect its vacancy, and may then assign another patient to the room. This is a significant improvement over the traditional verbal communication office network. This is just one example of improved efficiency offered by the invention.

Users may automatically be directed to certain pages related to their job assignments. Alternatively, users may define what is to be their homepage within the system. For example, a transcriptionist may be automatically directed to the dictation/transcription page upon logging in, or may set another system page as the default homepage. Help dialogue boxes may be displayed by positioning the mouse over or by selecting a help icon or by clicking help in the menu bar. Since the system is web based, conventional web browser application and menu functions are available on most any screen or window within the system. Any menu, list, or the like may include options to edit and expand listed options. Any blank list, screen, field, or dialogue box may include default language indicating that the field, file, etc. is empty.

Any number of features represented by different tabs, list item, links and the like, may be accessible from any number of interactive screens. Comments fields and standard menu or action links may likewise be cross-linked or associated with any displayed information, field, or other links. Entry of information in any of the described fields may be accompanied by a summary or confirmation page. As a web-based application, the system includes conventional browser and file menu options such as find, browse, edit, format and view functions. Auto-completion may be enabled for certain fields and defaults for others may be preset or user defined. For example, the current date may be automatically entered in any date field, yet still provide for alteration by a user.

Tabs, icons, list items, menu items, radio buttons, etc. may be used interchangeably and may be fully customizable, for example, as to number, title, contents, cross-references, and the like. Menu and pull-down lists may contain editing options such as "Edit this menu" or "Add new Item." Screens, windows, and dialogue boxes may refresh upon completion of certain tasks, upon depressing a mouse button or enter key, or may simply refresh at preset time intervals. Any window, screen, or document may be exported, printed, emailed, or saved. Passwords may be required for access at any given system level or feature providing increased security or privacy. For example, available options, features, and links may be determined by administrative authorizations assigned to individual users. Encryption may also be used to increase security.

Figure 3:
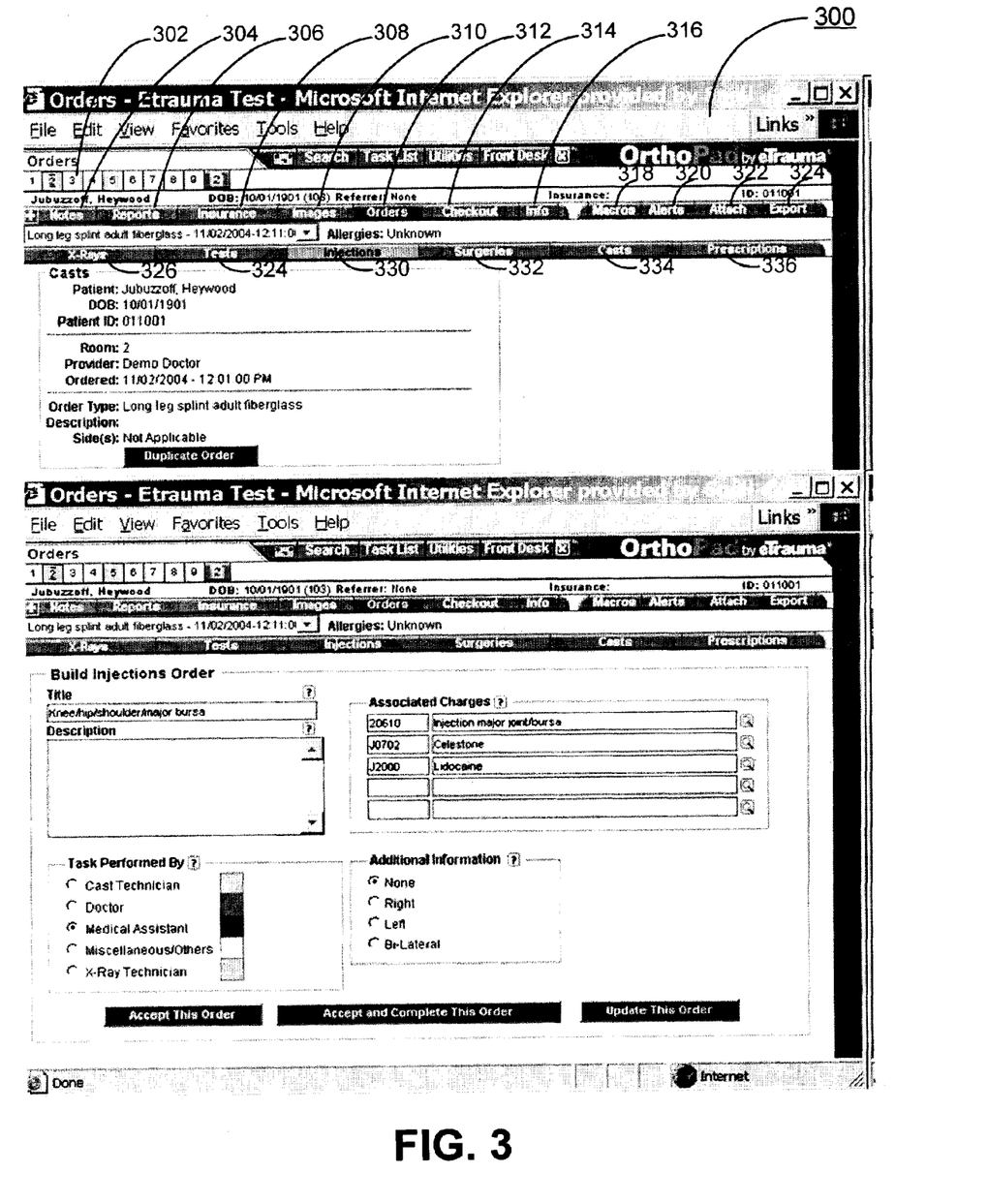
FIG. 3 is a screen shot of exemplary color coding and task scheduling systems.

FIG. 3 depicts an exemplary screen shot from a physician's Tablet PC showing an exemplary presentation of system features including the color coding and task management application features introduced above. Order page 300 includes selectable room identifiers 302, and selectable patient "chart" tabs: Notes 304, Reports 306, Insurance 308, Images 310, Orders 312, Checkout 314, and Info 316. Additional selectable screen features may include Macros 318, Alerts 320, Add Note 322, and Export 324. Each selectable tab, pull-down menu item, radio button, or other selectable feature may appear on more than one screen and may be customizable as to appearance, order, authorization, and the like as know in the art.

Selection of the Orders 312 tab returns additional tabs: X-rays 326, Tests 328, Injections 330, Surgeries 332, Casts 324 and Prescriptions 336. Each tab found under Order tab 312 may include any number of pull-down menus allowing a physician to readily select the desired tasks or procedures. For example, selection of X-ray tab 326 returns a screen having a number of fields, some including pull-down menus listing frequently x-rayed body parts (e.g. knee, elbow, ankle) and standardized views (e.g. AP/LAT, right, left, bilateral). Multiple x-rays orders may thus be submitted to the x-ray lab. The x-ray lab technician may thus instantly receive notice of the physician's order by the associated change in color of room identifier 302. Each room identifier 302 may be individually coded to reflect pending orders associated with the room and selection of any room identifier 302 may return a detailed listing of pending and/or completed orders. For example, order detail pages may include patient demographic information, procedures to be performed, associated charges, care provider, date and time of order, and who is to perform the ordered task. Interactive task buttons may allow technicians to accept an order, accept and complete an order, or update an order. Users may cancel orders as well. Associated charges for a completed order may be automatically placed in the patient's checkout sheet and billing statement.

Similarly, Test tab 328 displays pull-down menus offering MRIs, CTs, Epidurals, blood tests, and the like. Practitioners will appreciate that any number of different tests or procedures may be listed and organized according to the needs of a particular medical office. Injections tab 330 may provide lists of various body parts and injectable compounds for selection by a physician. It is contemplated that pharmaceutical applications may be integrated into the system to track current patient medications and to help doctors avoid incompatibilities in ordering medications or issuing prescriptions. The system may even suggest optional medications for various orders. Selection of Surgeries tab 332 provides lists of available procedures categorized, for example, by body part and then by related procedures. General applications that may be appreciated by those skilled in the art in light of the present disclosure are not described in detail herein.

Selection of Casts tab 334 provides lists of various casts, braces, and splints organized by body part. Selection of Prescriptions tab 336 provides selectable lists of prescriptions. Prescription orders may automatically be transmitted to the patient's pharmacy of record or to an onsite pharmacy terminal. It should be apparent, that any relevant task, procedure, medication, or other medical requirement may be similarly organized and offered in conjunction with any organizational hierarchy within the system.

Returning to the patient "chart" tabs set forth above, Notes tab 304 lists physician visit, diagnosis, and treatment notes. Reports tab 306 presents various completed task summaries and lab results and the like. Insurance tab 308 provides access to patient insurance information, such as a photocopy of the patient's insurance card. Images tab 310 provides access to any images such as x-rays, MRIs, CT scans, copies of insurance cards and the like. JPEG, TIFF, BITMAP, or other image formats may be used to store and display various patient images. The images need not be of diagnosis quality, but may serve only as a place holder or reference to the actual images on file with a particular x-ray or MRI lab. Different images may be selected for viewing just as document selection was described above.

Orders tab 312 has already been explored in detail above. Checkout tab 314 provides access to a checkout sheet listing additional interactive tabs labeled Diagnosis, Work Restrictions, Follow Up and Charges. A Diagnosis tab may include categorized and/or searchable ICD-9 diagnoses. A Work Restrictions tab may list varying work duty levels and recommended periods for different work duty levels to accommodate recuperation or disabilities. A Follow Up tab may list various return appointment times. A Charges tab may list various patient billing classifications. A Check-out Sheet may list orders, order status, order reports, and order charges.

Figure 5:
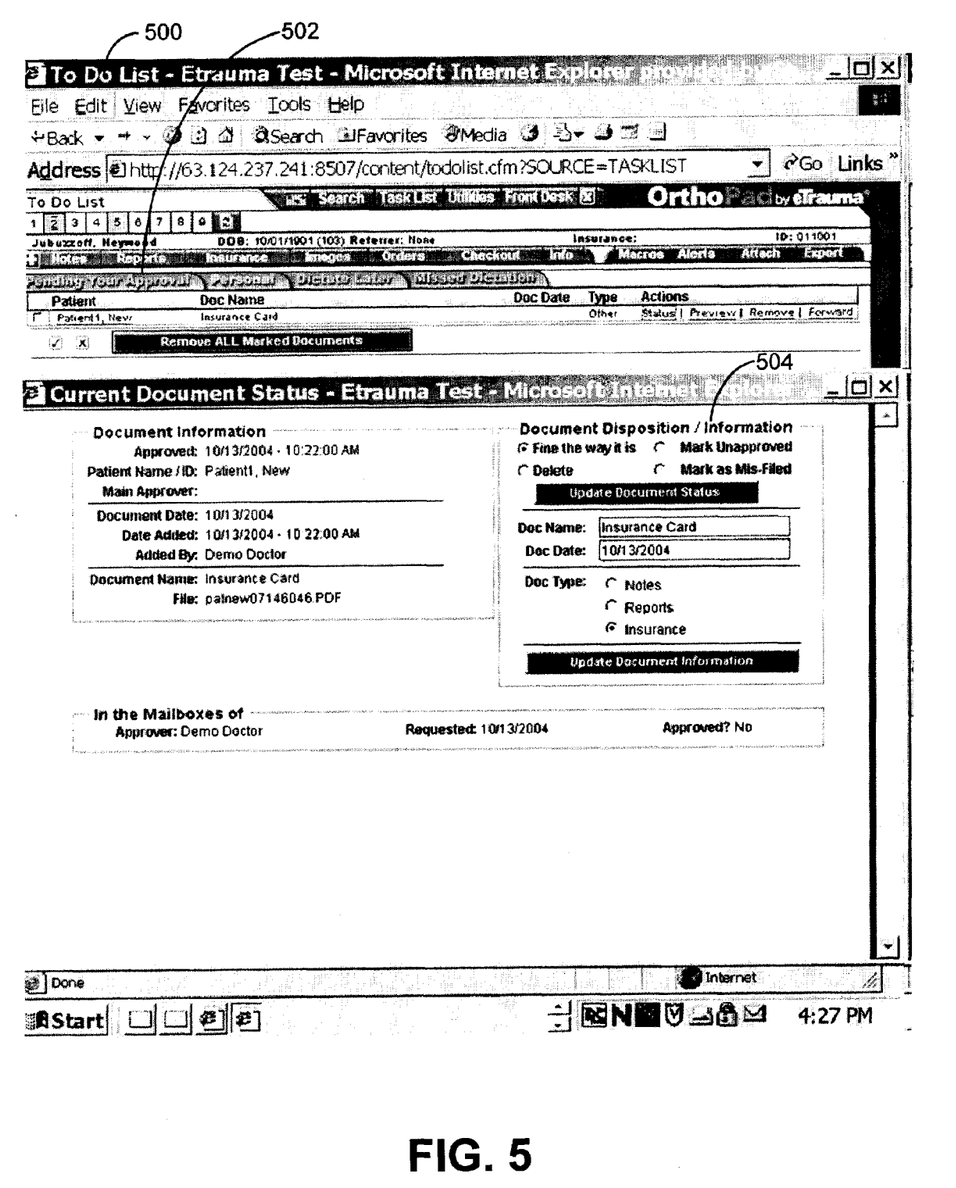
FIG. 5 is a screen shot of an exemplary documents management system.

Referring now to FIG. 5, the present system also provides improved efficiency in document management. For example, follow-up or doctor ordered paperwork can be generated or retrieved for delivery or doctor review even before the patient visit is over. The system may include a document management screen similar to "To Do List" 500. To Do List 500 may be part of a comprehensive electronic personal management and mailbox system similar to Microsoft Outlook®. A user may select from various document category tabs, such as, for example a "Pending Your Approval" tab 502, a "Personal" tab, a "Dictate Later" tab, a "Missed Dictation" tab, or any number of desired category tabs. Users reviewing documents under Pending Your Approval tab 502 may select from default or customized status or "Document Disposition" buttons 504 such as "Fine the way it is," "Delete," Mark Unapproved," and "Mark as Mis-filed" and may thus update the record accordingly. Documents may be associated with a patient file either before or after physician review. For example, documents may be automatically marked as "reviewed" and removed from a physician's Pending Your Approval mailbox list if an authorized physician views the document instead as part of the patient record.

The following description tracks the path or progress of a hypothetical user through an exemplary medical facility management system. To begin, a secure login page may require a unique user identification and password or any other secure authentication known in the art. The system may prompt users to alter their passwords from time to time to enhance security or may even suggest various examples of password progression schemes. Users may login at multiple terminals or alternatively an administrator may limit users to a single access point. Additional security may be provided by a timed logout or screen saver after a set period of inactivity. Users may logout manually by selecting or "clicking" a marker or icon such as the familiar X symbol found in the upper right hand corner of many applications. Any activity such as user logout, file deletion, visit or order cancellation may include confirmation screens or dialogue boxes to prevent inadvertent cancellations and the like. For example, a logout attempt may require confirmation by clicking "OK" or "Yes, logout" in a dialogue box. Additional security features may be provided in compliance with the federal HIPAA requirements. These features are variable by users to obtain the desired level of privacy and confidentiality according to office policies.

Successful login provides network or web access to a primary screen or "home page" listing at least one clinic or office ("location"). Locations may be listed in a drop-down or pull-down menu or as individual selectable tabs or icons. Selection of a location returns a list or visualization of all or select rooms at that location. A user may opt to continue without selecting any rooms. Any screen may provide links to any number of other interactive screens through a series of tabs, icons, links, menu, pull-down menus, and the like.

Figure 4:
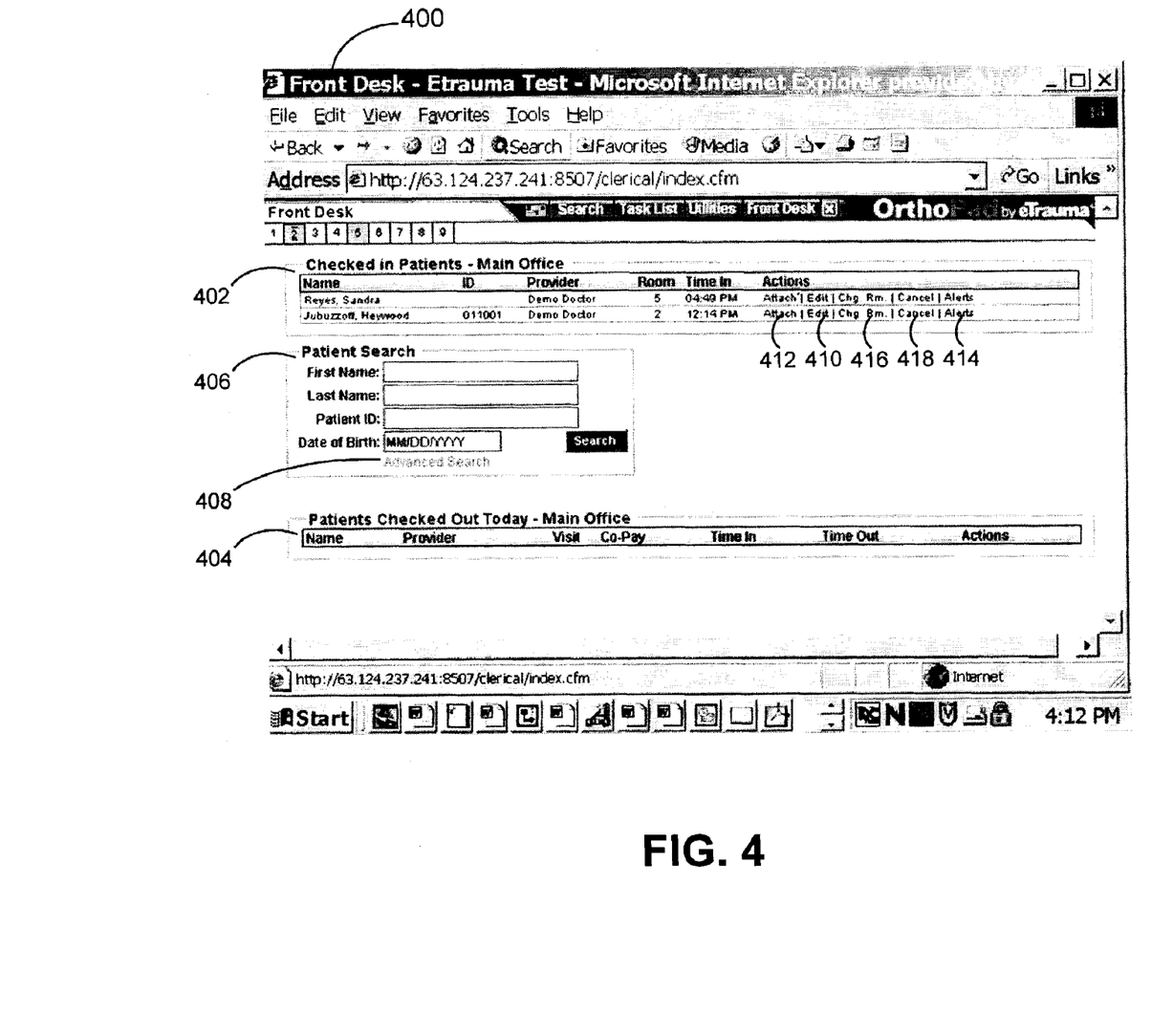
FIG. 4 is a screen shot of an exemplary front desk management system.

One such interactive screen may represent a clinic's "Front Desk" like that shown in FIG. 4. Staff at a clinic front desk may remain logged into the Front Desk 400 screen during clinic hours. Front Desk 400 screen includes fields or tables listing checked in patients 402, checked out patients 404, and a patient search field 406. Patient search field 406 may return patient records or patient status indicators based on entry of a patient's name, birthday, or alpha-numeric identifier or other demographic information. Searches may be conducted with only partial field entries, such as the first three letters of a patient name. Additional search options or searchable categories may be provided under an "Advanced Search" 408 option including fields for social security number ("SSN"), allergies, city, state, zip code, insurance carrier, phone number, email, comment, date added, or other searchable types of information used in the art.

A successful patient search may enable a "Check In" link that can be used to add the patient to Checked In list 402, as well as providing other "Actions" links. An unsuccessful patient search may enable an additional link titled "Click here to add a new patient." Clicking the link may return an Add Patient Record Form. Add Patient Record Forms may only require certain information such as first and last name, date of birth, allergies and co-pay or may include any number of optional fields. One optional field may provide for cross-references to patient ID numbers from preexisting management software. Other optional fields may include any of the advanced search fields described above, as well as referring physician information, comments, or any other customized field. This information is then submitted for electronic storage and processing. A patient information summary screen may be generated for confirmation. Once a new patient record is set up, any number of action links may be provided such as "Check In," "Upload documents for this patient," or "Return to front desk." Selection of "Check In" may prompt the user to select a provider and to enter a co-pay disposition.

Front Desk 400 displays Checked in Patients 402 field including names of patients, whether in a waiting room or exam room, as well as the corresponding provider, room number, and time elapsed. Various "Actions" links may associate certain editorial or operational functions with each patient. For example, an "Edit" 410 option may allow a user to alter information fields in a patient record. An "Attach" 412 option may associate additional records or tasks with a patient record. For example, clicking "Attach" 412 link may return an upload window where a user may browse to locate or simply enter a file name to be uploaded. An "Alerts" 414 link may list events or status changes for a particular patient. A similar link may list medical sensitivities such as allergies, medications, genetic family medical histories or life threatening conditions.

Staff may assign a patient in Checked In list 402 to a room by selecting an "Assign" link and/or checking a radio button corresponding to the desired room. A separate window may show the availability of various rooms, or a color coding system like that described above may be used to indicate room availability. A "Change Room" 416 link may allow staff to quickly reassign a patient to a new room. Similarly, a "Cancel" 418 link may be used to quickly remove patients from a field or list.

Front Desk Checked out Patients 404 fields may include the provider, total of patient visits, co-pay payment status, visit times, and the like. Associated "Actions" fields may include editing, attachment, or alerts options as described herein. Other "Actions" may include viewing or changing co-pay status/method, follow-up scheduling and accessing a patient checkout sheet. Checkout sheets may include fields and information such as ICD-9 Diagnoses, Charges, Work Restrictions, Follow-up Appointments and the like. Checkout sheets may be customizable to further include fields for Injections, Prescriptions, X-rays, Specialist Referrals, and Co-payments. Co-pay dispositions may list the amount and method of payment including, for example, check, charge, cash, bill later, or "not required." A "Reference Name or Number" field may be used to record a check number or credit card authorization number.

Paper documents may be scanned into any number of formats and associated with a patient file. For example, completed patient intake paperwork may be placed in a scanner and converted into PDF, JPEG, or other file formats. Audio files such as physician dictations may also be associated with a client file. Documents may be scanned for character object recognition. The files may then be named and associated with a patient file, or, alternatively may be automatically named based on manual or automatic association with a patient identifier. In other words, a file may be manually named and then attached or the document type may be specified and the remainder of the file name may be generated upon attachment to a particular patient file. A default folder such as a desktop "Scans" folder may be used to store converted files prior to naming and/or attachment. Preprinted forms may include enable character recognition software to automatically detect a document type (notes, reports, insurance, intake, check-out, privacy policy, etc) or even to automatically associate a scanned file to a patient file. Documents may also be assigned or "mailed" to a provider, any user, location, etc., for review or other tasks.

All system screens may include various standard tabs such as Search, Task List, Utilities, and Front Desk tabs along with a series of color coded room buttons. Patient specific tabs include Notes, Reports, Insurance, Images, Orders, Check-out, Info, Macros, Alerts, Add Note, and Export. A Provider Functions screen may be organized like a common paper chart with multiple tabs and buttons such as Room Number Buttons, Chart Tabs, Chart Buttons, Button Status, and Bringing Up a Chart button. Chart Tabs may include a Notes Tab, Reports Tab, Pull Down Menus, Right and Left arrows, Document Status Button, and Document Status Window. A Notes Tab may list intake documents and dictation transcriptions while a Reports Tab connects to MRI reports, Operation reports, etc. Pull-down menu lists may be used to list available documents under a given tab, for example in reverse chronological order. Documents may be selected for viewing from the pull-down menu by clicking on the document title, or on the on-screen arrows, or by use of the keyboard arrows. A "Doc Status" button may display the status of a document and allow user to make changes.

As described earlier, color coding or "flagging" of room identifiers such as Room Number Buttons may identify different providers, medical assistants, technicians, different tasks to be performed (e.g. x-ray, cast, therapy) as well as a room's status (vacant, occupied). For example, a first color indicates that the room is vacant, a second color indicates that a room is assigned to a provider, and a third color indicates that an Order has been placed with a particular lab or technician. Placing the cursor over a room may reveal additional information, including, for example, the name of a patient, the assigned provider, check-in time, and the next Order for the patient. Orders may include requests for x-rays, procedures, tests, casts, injections and prescriptions. A room may remain colored according to an Order until the Order is filled, even after a patient has been checked out. Clicking on a room number button may also bring up the chart for the patient assigned to that room. The last generated document or the last entered notes may appear first on this chart.

A user may select the desired Order from various pull-down menus as discussed earlier. Pull-down menus may be customizable to include additional Orders. Additionally, an Order preview screen is provided with fields for additional instructions, details, or notes. Providers may then select either an "Accept this Order" button placing the order in the Task List for back office staff to complete, or an "Accept and Complete This Order" button, in which case the task is marked as completed and is not placed on the Task List. Charges associated with different Orders may be automatically listed on the Checkout Sheet. Back staff may then indicate when an Order has been filled and a complete record, including notes, completion time, charges, etc., appears on the Orders screen. An "Update This Order" button may allow users to add or select task specific information and update the Order to reflect the changes. The available Orders lists and their titles may be fully customizable to suit users. For example, an "Add New Order" option provides access to an "Add Order" form with fields for pertinent information, including associated charges and assigning what user is to perform the task. Associated charges may be broken out into a number of categories, and may each receive a corresponding CPT code (Ex. 97806—Ankle X-ray). Added Orders may be for a single occurrence or may be added permanently to the drop-down list of Orders. Orders may likewise be deleted from the drop-down list of available Orders, which is different from canceling an Order after it has been placed. To Checkout a Patient, front desk staff may click a Checkout tab and select all pertinent items from the menus to display. The system may provide reminders when it detects that an office visit code has not been entered.

Once a patient file has been selected, users may be presented with various tab options including: Info, Alerts, Add Note, Export, Search, and Macros. The Info tab provides viewing or editing access to patient information. The Alerts tab lists events and provides reminders to staff of events that may not otherwise be part of the patient record. Alerts may be assigned different start dates, end dates or durations of hours, days, weeks, or months. Alerts may be categorized by type and may list Actions to be taken. These alerts may be viewed from both a Front Desk screen, a Checkout screen, and/or a patient's Chart screen. The Add Note tab allows for attachment of a document to a patient file or addition of notes to another user's mailbox. The Export tab allows a user to export a patient's chart including selected Notes, Reports, Studies, and Checkout Sheets. The Export feature may export various patient chart documents from different file formats into a single file, for example, in Adobe PDF format, with each page in the file representing an individual document in the chart. The Macros tab allows access to edit macro fields.

The system may provide each user a personal mailbox. Provider mailboxes may include additional organization or document management features such as the "Pending Your Approval," "Personal," "Dictate Later," and "Missed Dictation" tabs discussed earlier. For example, documents may be flagged for later review by a physician or may be automatically sent to the physicians "Pending Your Approval" folder. Any conventional email system options may be available through user mailbox accounts within the system. Users may alter the status of documents by selecting designators or options such as "Fine the way it is," "Delete," "Mark Approved," and "Mark as Misfiled." Misfiled documents may be sent to a "Clerical" mailbox to be properly filed. Approved documents may be electronically time/date stamped and removed from the Pending Approval list. Significantly, a document may be removed from the Pending Approval mail folder automatically when the authorized provider reviews the document in viewing the patient record. Documents may be approved individually or in batches. A warning may be displayed upon checkout if there are still unapproved documents associated with a patient record.

Task List Buttons show pending Orders listed by category (x-ray, cast, etc.) and then by time of the Order. Once a task is completed, the authorized user selects a Done button to reflect the new Order status, automatically triggering the addition of associated charges to the patient Checkout Sheet. A user assigned an Order may view the patient information by clicking on the Room button. Clicking a Cancel order button removes the Order from the list without placing charges on the Checkout Sheet. The Task List also lists patients who are checked in but who have not yet been assigned a room. Clicking the "Assign" link under the Room heading may provide a pop-up window for selection from available rooms.

A multiple transcription upload function may facilitate uploading of a single transcription file containing transcriptions for multiple patients, which are then split off into individual files for each patient, and automatically filed for each patient. The system separates individual patient transcriptions based on any number of available information fields such as patient name or account number. Transcriptions may be bounded by a set header with characters sets such as asterisks, or set terms such as "end doc" and "start doc." Blanket notes or additional headers may be applied to all transcriptions that follow in a file by placing the blanket information in a certain location (ahead of the first header), or between certain characters at the beginning of the document. System server integrity checks may be enabled to ensure that required fields, formatting, and characters are present before the server will allow document uploading. Additionally, minor errors may trigger error reports associated with the file, while not hindering an upload. Documents with error reports may be placed in an unassigned transcription folder for manual attaching. HTM format files created by Microsoft Word or other formats known in the art may be used. All transcriptions may thus be automatically placed into a physicians system mailbox for approval.

A Utilities Functions screen may display various task buttons including "Billing/Encounter Points," "Work With Unassigned Documents," "Upload a Document for Review," "Checkout Reports," "Reset Room," "Search SPT Codes," "Search ICD-9 Codes," "Edit Macros," and "Edit Orders Menus."

The Billing/Encounter Points button provides access to Checkout Sheets for billing purposes. Checkout Sheets may be retrieved or ordered by various criteria such as location, provider, and/or date and may selectively include associated documentation such as intake documents, office visit notes, previous bills and the like. Reported information may then constitute a record of the patients visiting a medical facility over a particular time period. Such information may be useful, for example, for later recounting the list of patients who have visited on a particular day and time, a particular patient visit, tracking the number of patients seen during a particular time frame, or the like. The Work With Unassigned Documents button allows for review of uploaded documents that are not yet assigned to a patient record. This area may have numerous subsections such as faxes, transcriptions, and uploaded documents. Faxes may be automatically converted (as with the Right Fax product) to PDF format and delivered to the mailbox of a designated recipient. Documents from any of the subsections may be attached to a patient record, deleted, stored, edited, replaced, or sent to user mailboxes.

The Upload a Document for Review button allows for uploading of documents (administrative and personal documents) to the server without attaching them to a patient record. The Checkout Reports button generates copies of checkout reports for use by accounting or administration. The reports may be categorized by location, provider and/or date. The Reset Room button may be used to correct the status of a vacant room that is incorrectly shown as occupied, possibly due to multiple room assignments, incorrect checkout, or other causes. The Search CPT and ICD-9 Codes buttons allows users to search and assign proper payment codes and costs, including the latest Medicare conversion factor and geographic region calculations. The Macros button is a time saving feature allowing users to establish sets of orders or tasks to be executed by a single command. For example, a physician may initiate a set of predefined Orders with a single click. The Edit Orders Menus button allows users to categorize menus and submenus under both the orders and checkout areas by editing, adding, and deleting listed orders. For example, an added order may be titled and may include a description of what is to be accomplished, who is to perform the described tasks and set out the associated charges.

An "Alerts" feature may be used to remind office staff of particular patient events. For example, a patient alert may signal that there are to be no additional office visit charges for 90 days following a particular operation. The staff then knows when to begin collecting co-payment and to continue billing. Similar alerts may indicate when a referral expires or when a past visit remains unpaid. Alerts may optionally become part of the patients permanent record. Alerts may be set by clicking the "Alerts" link next to a patient name in a chart. The user then enters the start date, end time/date, the text of the alert, and whether it is to be displayed on the Check-in, Checkout, or other screens.

Although the present patient invention is described with respect to medical facilities management (e.g., patient/room and patient records management), the invention is not so limited. That is, it is contemplated that the invention may be used to manage any similar facility having a flow of patients or clients and associated documentation.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the invention is accordingly to be limited by nothing other than the appended claims. All structural and functional equivalents to the elements of the above-described exemplary embodiments that are known to those of ordinary skill in the art are expressly incorporated herein by reference and are intended to be encompassed by the present claims. Further, no element described herein is required for the practice of the invention unless expressly described as "essential" or "critical."

It should be understood, however, that the detailed description and specific examples, indicating exemplary embodiments of the invention, are given for purposes of illustration only and not as limitations. Many changes and modifications within the scope of the instant invention may be made without departing from the spirit thereof, and the invention includes all such modifications. Corresponding structures, materials, acts, and equivalents of all elements in the claims below are intended to include any structure, material, or acts for performing the functions in combination with other claim elements as specifically claimed. The scope of the invention should be determined by the appended claims and their legal equivalents, rather than by the examples given above.

What is claimed is:

1. A computer-implemented medical facilities management system comprising:
    at least one user interface configured to display a color-coded room identifier for an examination room and transmit user input to a server over at least one network, wherein the at least one user interface is configured to receive user input indicating a first ordered medical task and a second ordered medical task associated with a patient assigned to the examination room; and
    a server hosting a web-based medical office management software application coupled to said at least one user interface over the at least one network, wherein said office management application is configured to,
        assign to the displayed room identifier, a first color associated with the first ordered medical task, and automatically update the displayed room identifier to the first color,
        receive an indication that the first ordered medical task is complete, from at least one user interface,
        upon receiving the indication that the first ordered medical task is complete, automatically assign the displayed room identifier a second color associated with the second ordered medical task and automatically update the displayed room identifier,
        receive an indication that the second ordered medical task is complete, from at least one user interface,
        upon receiving the indication that the second ordered medical task is complete, automatically assign the displayed room identifier a third color indicating that all tasks among a plurality of tasks are complete and automatically update the displayed room identifier to the third color,
        receive a selection of the room identifier from at least one user interface, and
        in response to receiving the selection, transmit a list to at least one user interface, the list including the first ordered medical task and the second ordered medical task.

2. The system of claim 1, wherein said room identifier is color coded according to whether said first ordered medical task is at least one of assigned, scheduled, begun, performed, suspended, completed, and reported by at least one of medical care providers, medical staff, office staff and medical technicians.

3. The system of claim 1, wherein said office management application is further configured to facilitate color coding of examination room identifiers according to examination room status of at least one of vacant, occupied, patient checked-in, patient checked-out, physician occupied, in need of cleaning, and out-of-use.

4. The system of claim 1, wherein said office management application is further configured to facilitate color coding of examination room identifiers according to an identity of at least one of a care provider, assistant, technician, medical staff member, and office staff member assigned to at least one of a room, an ordered medical task, and a patient associated with said examination room.

5. The system of claim 1, wherein said at least one user interface is rendered on a user terminal that is at least one of a desktop computer, laptop computer, tablet PC, handheld device, and a cellular phone.

6. A computer-implemented method of communicating information about an examination room of a medical facility, the method comprising:
   hosting, by a host server, a web-based medical office management software application that displays a room identifier for the examination room, the web-based application accessible by at least one user terminal over at least one network;
   receiving, through the web-based application over the at least one network, by the host server, user input that specifies a first ordered medical task and a second ordered medical task for a patient assigned to the examination room;
   assigning, by the host server, to the displayed room identifier, a first color associated with the first ordered medical task, and automatically updating, by the host server, the displayed room identifier to the first color;
   receiving, through the web-based application over the at least one network, by the host server, an indication that the first ordered medical task is complete, from at least one user terminal;
   upon receiving the indication that the first ordered medical task is complete, automatically assigning, by the host server, the displayed room identifier a second color associated with the second ordered medical task and automatically updating, by the host server, the displayed room identifier;
   receiving, through the web-based application over the at least one network, by the host server, an indication that the second ordered medical task is complete, from at least one user terminal;
   upon receiving the indication that the second ordered medical task is complete, automatically assigning, by the host server, the displayed room identifier a third color indicating that all tasks among a plurality of tasks are complete and automatically updating, by the host server, the displayed room identifier to the third color;
   receiving, by the host server over the at least one network, a selection of the room identifier from at least one user terminal; and
   in response to receiving the selection, transmitting, by the host server over the at least one network, a list to at least one user terminal, the list including the first ordered medical task and the second ordered medical task.

7. The computer-implemented method of claim 6, further comprising coding room identifiers differently on different user terminals to convey information specific to an ordered medical task to which the respective user terminal corresponds.

8. The computer-implemented method of claim 6, further comprising:
   automatically recording associated charges for the first and second ordered medical tasks for billing upon completion of the first and second ordered medical tasks.

9. The computer-implemented method of claim 6, further comprising:
   coordinating a color of said at least one room identifier according to at least one of patient medical condition, patient medical alerts, and completed ordered medical tasks.

10. A host server comprising a processor and a memory coupled to the processor, wherein the host server is configured to execute a computer-implemented method of communicating information about an examination room of a medical facility, the method comprising:
   hosting, by the host server, a web-based medical office management software application that displays a room identifier for the examination room, the web-based application accessible by at least one user terminal over at least one network;
   receiving, through the web-based application over the at least one network, by the host server, user input that specifies a first ordered medical task and a second ordered medical task for a patient assigned to the examination room;
   assigning, by the host server, to the displayed room identifier, a first color associated with the first ordered medical task, and automatically updating, by the host server, the displayed room identifier to the first color;
   receiving, through the web-based application over the at least one network, by the host server, an indication that the first ordered medical task is complete, from at least one user terminal;
   upon receiving the indication that the first ordered medical task is complete, automatically assigning, by the host server, the displayed room identifier a second color associated with the second ordered medical task and automatically updating, by the host server, the displayed room identifier;
   receiving, through the web-based application over the at least one network, by the host server, an indication that the second ordered medical task is complete, from at least one user terminal;
   upon receiving the indication that the second ordered medical task is complete, automatically assigning, by the host server, the displayed room identifier a third color indicating that all tasks among a plurality of tasks are complete and automatically updating, by the host server, the displayed room identifier to the third color;
   receiving, by the host server over the at least one network, a selection of the room identifier from at least one user terminal; and
   in response to receiving the selection, transmitting, by the host server over the at least one network, a list to at least one user terminal, the list including the first ordered medical task and the second ordered medical task.

* * * * *